United States Patent [19]

Riordan

[11] Patent Number: 4,912,039
[45] Date of Patent: Mar. 27, 1990

[54] MULTIDRUG RESISTANCE IN MAMMALIAN CELL LINES AND ISOLATION OF DETERMINANT GLYCOPROTEIN DNA

[75] Inventor: John R. Riordan, Toronto, Canada

[73] Assignee: HSC Research Development Corporation, Toronto, Canada

[21] Appl. No.: 774,368

[22] Filed: Sep. 10, 1985

[30] Foreign Application Priority Data

Sep. 10, 1984 [GB] United Kingdom ............... 8422819
Sep. 3, 1985 [CA] Canada ........................... 489897

[51] Int. Cl.$^4$ ............... C12P 21/00; C12P 19/34; C12N 15/00; C12N 1/20
[52] U.S. Cl. ................... 435/69.1; 435/91; 435/320; 435/252.33; 435/172.3; 935/11; 935/12; 536/27
[58] Field of Search ............ 536/27; 435/68, 320, 435/172.3, 253, 91, 252.33; 935/6, 11, 12

[56] References Cited

PUBLICATIONS

Riordan et al., Nature, 316, pp. 817–819 (8–1985).
Roninson et al., Proc. Natl. Acad. Sci., 83, pp. 4538–4542 (1986).
Gros et al., Nature, 323, pp. 728–731 (1986).
Young et al., Proc. Natl. Acad. Sci., 80, pp. 1194–1198 (1983).
Choate et al., "Patent Law", pp. 1112–1115, West Publishing, 1981.
Kartner et al., (1983), Science, 221: 1285–88.
Riordan et al., (1979), J. Biol. Chem., 254(24) 12701–05.
Kartner et al., (1983), Cancer Research, 13:4413–19.
O'Hara et al., (1982), Immuniol. Lett., 5(1), 15–18 (abstract).
Urdea et al., (1983), "Chemical Synthesis of . . . ", PNAS 80: 7461–65.
Roninson et al., "Amplification of Specific DNA Sequences Correlates with Multi-Drug Resistance in Chinese Hamster Cells", Nature, vol. 309, pp. 626–628 (1984).

*Primary Examiner*—John Edward Tarcza
*Attorney, Agent, or Firm*—Banner, Birch McKie & Beckett

[57] ABSTRACT

A method for isolating a cDNA specific for P-glycoprotein is disclosed. The P-glycoprotein is the determinant in the multidrug resistance phenotype exhibited by living cells. The nucleic acid equivalent of the cDNA may be cloned in a recombinant plasmid or phage. The cDNA may also be used as a probe in determining multidrug resistance in cells. The DNA molecules specific for the P-glycoprotein is in the form of a gene family where various members of the gene family are amplified to varying degrees in multidrug resistant cells from various sources.

37 Claims, 4 Drawing Sheets

MULTIDRUG RESISTANCE IN MAMMALIAN CELL LINES AND ISOLATION OF DETERMINANT GLYCOPROTEIN DNA

FIELD OF THE INVENTION

This invention relates to living eucaryotic cells developing resistance to drugs which are normally toxic to them and more particularly, to the determinant of drug resistance of living cells and the nucleic acid sequence encoding for the protein determinant.

BACKGROUND OF THE INVENTION

It is known that mammalian cells develop resistance to drugs, such as discovered in the field of cancer research where cancerous cells develop resistance to drugs used in chemotherapy. This resistance halts the effectiveness of the drugs used in chemotherapy for slowing down or ceasing the multiplication of the cancerous cells. Recently reported in *Science*, Vol. 221, pp 1285–1288, Sept. 1983, reference is made to hamster, mouse and human tumerous cell lines displaying multiple drug resistance. It was discovered that there is an increased expression of a 170,000-dalton surface antigen correlated with multidrug resistance as found in the cell membrane. The antigen has been isolated and is understood to be a P-glycoprotein.

Multidrug resistance (MDR) is the phenotype exhibited by mammalian cell mutants particularly selected for resistance to a certain anti-cancer drug, but also exhibiting resistance to a broad spectrum of other cancer drugs having different chemical structures and targets of action. Cells with this phenotype maintain reduced intracellular levels of drugs as the apparent mechanism of resistance. Related to this altered drug transport function, the plasma membranes of these cells contain elevated amounts of the polypeptide specifically referred to as P-glycoprotein.

It has been possible to select a variety of mutant cell lines with different degrees of drug resistance. The amount of P-glycoprotein in the plasma membranes of these different cell lines correlates quantitatively with the degree of drug resistance.

Over-expression of P-glycoprotein appears to be a consistent and characteristic feature of the multidrug resistance phenotype.

Extensive work has been conducted to demonstrate this P-glycoprotein directly or indirectly mediates the multidrug resistance phenotype. Extensive genetic studies have been carried out on Chinese hamster ovary cell systems as disclosed in Ling V., Kartner, N., Sudo, T., Siminovitch, L. and Riordan, J. R. *Cancer Treat. Rep.* 67, 869–874 (1983). In these studies, it is established that:

(a) independent drug resistant clones isolated in the single step without mutagenesis display the multidrug resistance phenotype and P-glycoprotein over-expression;

(b) selection for increased drug resistance, i.e., colchicine resulted in increased cross-resistance to other drugs and increased P-glycoprotein expression;

(c) revertants isolated in a single step for drug sensitivity to one compound involved in the multidrug resistance phenotype, displays reversion of the other aspects of the phenotype including reduced P-glycoprotein expression;

(d) cross-resistance, collateral sensitivity, and P-glycoprotein over-expression are concordantly expressed in cell:cell hybrids.

The unknown aspect with respect to the isolation of the P-glycoprotein and its determinant in causing multidrug resistance is whether or not a protein of this size is coded by a single gene or family of genes or the result of independent events in the selective expression of a gene or gene family.

SUMMARY OF THE INVENTION

According to an aspect of the invention, an essentially pure DNA molecule codes for a polypeptide moiety of a P-glycoprotein having a molecular weight of approximately 170,00 daltons.

According to another aspect of the invention, an essentially pure nucleotide sequence of the DNA molecule codes for a corresponding polypeptide sequence of the P-glycoprotein. The nucleotide sequence may be constructed of cDNA, mRNA or a fragment of DNA which codes for a corresponding portion of the polypeptide sequence. The nucleotide sequence may be incorporated in recombinant form with a bacterial phage or plasmid. The phage or plasmid may be cloned and when transformed in a suitable host, the host may be cultured to produce corresponding polypeptide sequences of the P-glycoprotein.

According to another aspect of the invention, the nucleotide sequence in the form of a bacterial phage and/or plasmid may be used as a DNA probe with suitable marker provided on the phage or plasmid.

According to another aspect of the invention, a method for isolating in a plasmid the cDNA comprises constructing a cDNA library using a known phage expression vector and mRNAs obtained from highly drug resistant cell lines which over-express the P-glycoprotein. By appropriate techniques, such as the use of monoclonal antibodies, the phage vectors which express a fusion protein antigenic to an antibody, which is specific to the P-glycoprotein, are identified. A recombinant plasmid is formed from the identified phages. The plasmid is expressed in a compatible living cell to produce a corresponding polypeptide sequence. The antibody is used to confirm that the polypeptide sequence is a portion of the P-glycoprotein.

BRIEF DESCRIPTION OF THE DRAWINGS

Preferred embodiments of the invention are discussed with respect to the drawings, wherein;

FIG. 3a is a Southern blot analysis of EcoRl digested genomic DNA from the same series of increasingly multidrug-resistant CHO cells as in FIG. 2a;

DETAILED DESCRIPTION OF THE PREFERRED EMBODIMENT

Methods have been developed for the isolation and characterization of plasma membrane vesicles which serve as the starting material for the purification of P-glycoprotein. The protein has been purified and characterized as an intrinsic glycoprotein having a polypeptide moiety of a molecular weight of 140 kilodaltons and as a corresponding P-glycoprotein having a molecular weight of 170 kilodaltons and an isoelectric point of about 7.4. Polyclonal and monoclonal antibodies to the protein have been raised.

The developed monoclonal antibodies specific for and which strongly cross-react with the glycoprotein from different species are used to screen living cells which include the glycoprotein as part of the membrane. A complementary DNA (cDNA) library may be constructed from messenger RNA (mRNA) from the highly drug resistant cell line which overexpresses the glycoprotein. The library may be constructed by using the expression vector λgtll. Phage plaques expressing β-galactosidase fusion proteins antigenic to the monoclonal antibody specific for P-glycoprotein are identified, picked and analyzed in an attempt to locate a cDNA encoding for a polypeptide sequence of the P-glycoprotein.

Membrane proteins from different multidrug resistant lines have been immunoblotted with polyclonal antibodies specific for P-glycoprotein as disclosed in Science Vol. 221 supra. The degree of P-glycoprotein expression has been found to correlate with the relative drug resistance of the cell lines. Thus, the over-expression of P-glycoprotein appears to be the most consistent molecular marker associated with the multidrug resistance phenotype for living cells. It has been found that there is over-expression of P-glycoprotein in biopsy samples obtained directly from tumour cells of ovarian patients with advanced ovarian tumours which were non-responsive to chemotherapeutic treatment.

In order to isolate the nucleic acid sequence encoding for the polypeptide segment isolated by use of the monoclonal antibody, the complementary DNA library is constructed. One of the raised monoclonal antibodies (C219) to the P-glycoprotein is used to screen this library for clones which synthesize β-galactosidase-P-glycoprotein fusion products. Several phages were identified and plaque purified.

One of the presumptive glycoprotein cDNA clones, now in the form of λ CHP-1 was isolated and subcloned in the plasmid pUC-9 to yield the plasmid pCHP-1. This cloned plasmid has an insert of approximately 600 base pairs which can be used as a probe for molecular hybridization analysis of nucleic acid sequences from drug resistant and drug sensitive cells. The insert of the plasmid pCHP-1 of approximately 600 base pairs encodes from the carboxyl end of the protein at least a portion of the P-glycoprotein which is over-expressed in the isolated drug resistant cell. In using the nucleic acid sequence as a probe for determining if cells are developing drug resistance, the nucleic acid sequence may be labelled with a detectable marker. The marker may be in the form of a label which is radioactive, fluorescent or biotinylated.

According to this invention, for purposes of cloning the plasmid pCHP-1, the plasmid may be transformed into a host microorganism for purposes of making multiple copies of the plasmid. The microorganism may be a strain of E. coli which acts as the host cell for the cloning vehicle. The polypeptide, which is a part of the P-glycoprotein as the determinant factor in cell resistance to drugs, may be produced by culturing the host microorganism or any other organism into which the cloning vehicle is transformed.

The host cell for the cloning vehicle, according to an embodiment of this invention, is the strain JM83 of E. coli K-12, Messing, J., Recombinant DNA Technical Bulletin, NIH Publication No. 79-99, 2, No. 2 (1979) 43-48. This host cell with the novel plasmid may be obtained through ATCC accession No. 39839 deposited on Sept. 7, 1984. This host cell contains a recombinant plasmid, pCHP-1. This plasmid was constructed by insertion of a cDNA sequence corresponding to a portion of the coding sequence of the P-glycoprotein into the unique EcoRl cloning site of the plasmid cloning vector, pUC9 (Vieira, J. and Messing, J., Gene, 19 (1982) 259-268).

The cDNA clone pCHP-1 codes for a C-terminal segment of P-glycoprotein consisting of approximately two hundred amino acid residues. The DNA insert in this clone is estimated to be about 650 bp in length. The fusion product consisting of the polypeptide coded for by at least a portion of this sequence plus β-galactosidase has a size of about 140,000 daltons. Subtraction of the β-galactosidase molecular weight of 116,600 daltons yields 23,400 daltons as the molecular weight of the peptide coded for by the insert sequence. This represents about 190 amino acid residues or 570 bp. Therefore, all but about 80 bp of the insert are required to code for the peptide. These 80 bp must represent a portion of the 3' untranslated sequence.

pCHP-1 was used to re-screen the same lamda library and five additional cDNA clones were obtained. These had sizes of 1.2; 1.3; 1.65; 2.0 and 2.5 kb. The longest which codes for approximately one half of complete P-glycoprotein polypeptide was designated pCHP-2 and deposited with ATCC on July 30, 1985 and given accession No. 53234.

It is appreciated, however, that with extensive exacting procedures the nucleic acid sequence for the polypeptide portion of the P-glycoprotein is isolated by selecting mammalian cell lines which exhibit resistance to drugs, such as adriamycin, actinomycin D, colchicine, daunorubicin, emetine, podophyllotoxin, puromycin, taxol, vinblastine or vincristine, all of which frequently exhibit a pleiotrophic phenotype of multidrug resistance. This complex phenotype involves cross-resistance to structurally and functionally unrelated compounds. Although the plasma membrane of the cell is implicated in this complex phenotype of drug resistance by the cell, the actual mechanisms involved are not fully understood. According to an embodiment of the invention, the extensive procedures for isolating the nucleic acid sequence of the P-glycoprotein gene include selection of multidrug resistant mutant cells; their genetic characterization; drug transport studies; plasma membrane characterization including isolation of a P-glycoprotein to which antibodies are prepared. The antibodies are then used to screen a bacteria phage cDNA expression vector library prepared from the mRNA isolated from highly multidrug resistant mutants and the positive recombinant bacteria phage clones identified can then be used to subclone the P-glycoprotein specific DNA sequence into a plasmid vector. In this manner, the entire P-glycoprotein gene can be isolated and characterized.

It is appreciated that a segment isolated and cloned in plasmid pCHP-1 may include encoding regions which are not operable in coding for the polypeptide segment of the P-glycoprotein. It is believed that the operative portion of the nucleic acid insert has approximately 600 pairs of the approximately 650 base pairs which may be in the recombinant plasmid pCHP-1. As established and shown in FIG. 1, the protein moiety of P-glycoprotein is about 140,000 daltons which would require a messenger RNA with a coding region of about 4 kb. In cells with over-expression of the P-glycoprotein, the single major mRNA component is of about 5 kb. The difference in weight is due to the 5' and 3' untranslated regions of the mRNA which would increase the size of the P-glycoprotein mRNA to about 5 kb.

The polypeptide determinant for drug cell resistance is identified as a P-glycoprotein having a molecular weight in the range of 170,000 daltons. The concentration of the cell surface glycoprotein is quantitatively correlated with the multidrug resistance phenotype in the CHO cell system under a variety of conditions. Highly resistant lines have increased expression of P-glycoprotein in the cell membrane. This membrane component appears to be overexpressed in other multidrug resistant lines isolated in animal and human cells. At least part of the P-glycoprotein molecular is highly conserved; i.e., constant among P-glycoprotein in different species. The monoclonal antibodies raised strongly cross-react with P-glycoproteins from different animal and human cells.

The monoclonal antibody (C219), which was used to identify λgt11 clones containing P-glycoprotein sequences, was raised using isolated plasma membrane vesicles, which were prepared as described in Riordan, J. R. and Ling, V. (1979) "Purification of P-Glycoprotein from Plasma Membrane Vesicles of Chinese Hamster Ovary Cell Mutants with Reduced Colchine Permeability", *J. Biol. Chem*, 254: 12701–12705, from highly colchine resistant CHO cell line (B30) as immunogen. Mice were immunized with these vesicles. After several booster injections, cells from the spleens of the mice were fused with a myeloma cell line to produce a battery of hybridoma cells. These were screened for the production of antibodies to the P-glycoprotein vesicles of multidrug resistant cells, but not those from drug sensitive cells.

Figure 2A:
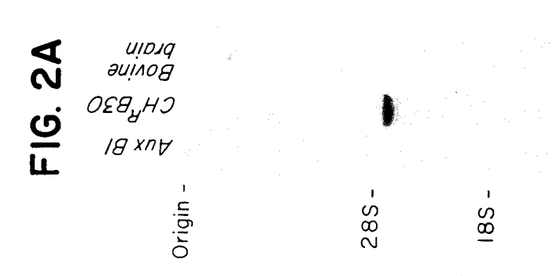
FIG. 2a is Northern blot analysis of total cellular RNA from drug sensistive flux B1 cells and highly multidrug resistant B30 cells, the third lane containing RNA from normal bovine brain serves as a control.
Figure 2B:
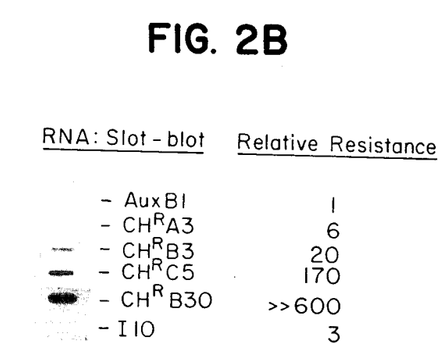
FIG. 2b is Slot blot analysis of RNA from a series of cells with varying levels of drug resistance similar to those in FIG. 1, the relative degrees of resistance being indicated opposite each slot.

Cell lines of increased drug resistance have increased P-glycoprotein expression. FIG 2b shows Slot blots of mRNA prepared from a related series of $CH^R$ clones with increasing drug resistance, AuxB1 →$CH^RA3$ →$CH^RB3$ →$CH^RC5$ → → →$CH^RB30$ as well as the revertant clone I10 which was selected from $CH^RC5$. The amount of mRNA revealed by the pCHP-1 probe in these cell lines is consistent with the levels expected if pCHP-1 sequences encoded a portion of P-glycoprotein.

Figure 3A:
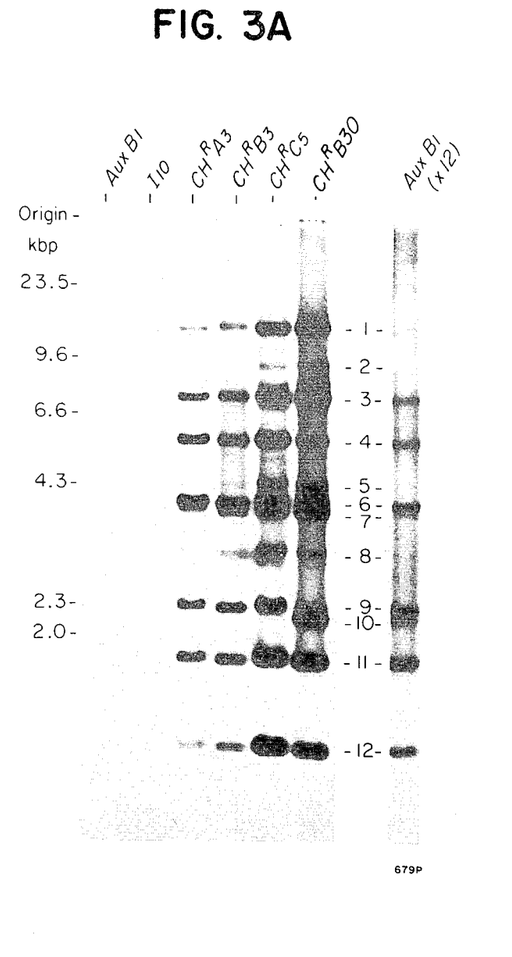
Figure 3B:
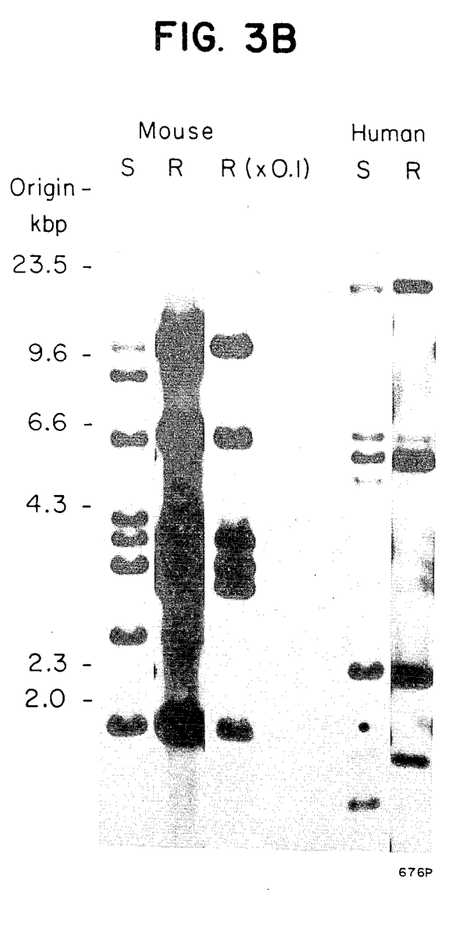
FIG. 3b is a Southern blot analysis of EcoRl digested DNA from drug sensitive human leukemic cell line (CEM) and a multidrug resistant variant (CEM/Vlb1000). The other pair are from drug sensitive mouse L cells (LMTK−) and MDR variant (ECH$^R$). Methods were as in FIG. 2b.

Southern blot analysis of genomic DNA from the drug sensitive and series of related multidrug-resistant $CH^RCHO$ cell lines of FIG. 2b is shown in FIG 3a. It is clear that sequences homologous to pCHP-1 are amplified in the resistant lines compared with the drug-sensitive or revertant lines. Moreover, the amount of amplification correlates with increased drug resistance. This indicates that over-expression of P-glycoprotein in these lines resulted from gene amplification. There appears to be ten EcoR1 fragments ranging in size from 1 to 15 kb homologous to pCHP-1 in the genome of the drug-sensitive cell lines. Multiple bands are also observed when other restriction enzymes were used (data not included in FIG. 3a). Multiple bands may result if the pCHP-1 probe were to span more than one exon; however, since the pCHP-1 probe does not have internal EcoR1 sites, and since the insert size is only about 600–700 bp, the multiple bands observed in FIGS. 3a and 3b are likely the result of the presence of a family of genes coding for corresponding P-glycoproteins all of approximately the same molecular weight. The P-glycoprotein gene family appears to be clustered within one amplifiable unit (an amplicon). This is supported by the observation that in the clonal line selected for resistance to colchicine in a single discrete step, e.g. $CH^RA3$ of FIG. 2b, simultaneous amplification of the ten restriction fragments occurred. Moreover, each fragment is amplified nearly equally by about 10–20 fold when compared with the equivalent fragment in the drug-sensitive line. In other systems, amplicons have been estimated to be approximately 100 to 1,000 kbp in size, thus the P-glycoprotein gene family is believed to be organized in a tandem array within such a region. A similar coordinate increase in amplification of P-glycoprotein genes is not observed in the second-step clone ($CH^RB3$), the third-step clone ($CH^RC5$), or the multi-step line ($CH^RB30$). The restriction pattern becomes more complex, and the degree of amplification among the different restriction fragments appears to vary to a greater extend. In $CH^RB30$ for example, restriction fragments 4, 6, and 9 were amplified by 10–20 fold, while fragments 7, 10, 11, 12 were amplified 50 fold or more as shown in FIG. 3a. These numbers were estimated by quantitative densitometry of appropriately exposed films in a separate experiments. Of interest was the appearance of amplified fragments in the more resistant lines which were not represented in the parental DNA. Examples of these are fragments 2 and 5 of FIG. 3a. These may represent "novel joint" regions found in tandemly amplified sequences as described in Stark, F. R. and Wahl, G. M. *Ann. Rev. Biochem.* 53, 447–491 (1984).

The above observations indicate the CHO cell genome contains a family of as many as ten P-glycoprotein genes which are linked, and that this gene family is amplified in colchicine-resistant, multidrug-resistant cell lines. Southern blot analysis of multidrug-resistant mouse and human lines using pCHP-1 demonstrated that P-glycoprotein sequences in these species are also encoded by a family of genes and that some members of the family are amplified in the resistant lines as shown in FIG. 3b. Eight EcoR1 fragments containing distinct P-glycoprotein gene sequences of the family are observed in the mouse genome. Five of these fragments are clearly amplified in the resistant line; however, the other three fragments migrating just below the 9.6 kb and 4.3 kb marker, and just above the 2.3 kb marker, are apparently not amplified. Similarly, in the human genome eight fragments are observed but only four of the eight fragments are clearly amplified in the resistant line. The finding that some of the EcoRl fragments are apparently not amplified in both mouse and human resistant cell lines suggests that the P-glycoprotein genes in these lines may not be contained in a single amplicon and may be dispersed, in contrast to what was observed in CHO cells. In the resistant mouse cells a new fragment of about 3 kb not present in sensitive cells is observed as shown in FIG. 3b. This is consistent with a "novel joint" region in the tandemly amplified sequences as mentioned above. Such a fragment is not observed in the resistant human line. The fact that pCHP-1 is able to hybridize strongly to the presumptive human P-glycoprotein sequences under stringent conditions provides further confirmation that P-glycoprotein is conserved both at the protein and DNA level.

Figure 4A:
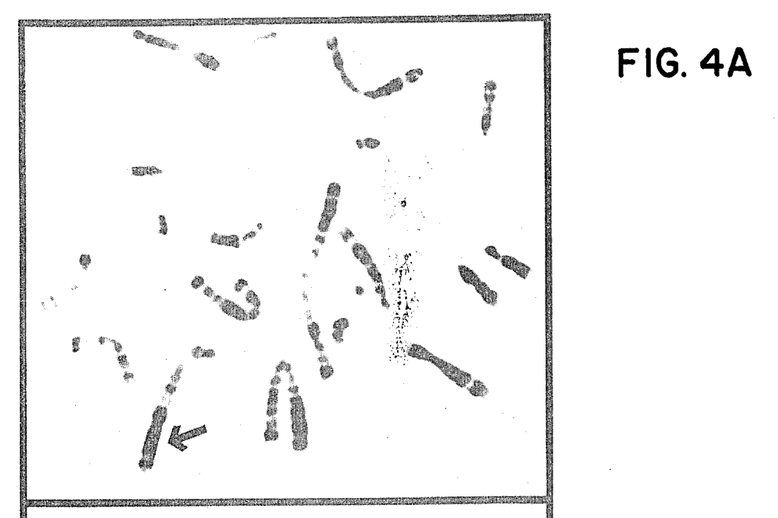
FIGS. 4a, b and c show cytological evidence for localization of P-glycoprotein sequences to a homogeneously staining region on the Z4 chromosome of CHO cell line B-30.
Figure 4B:
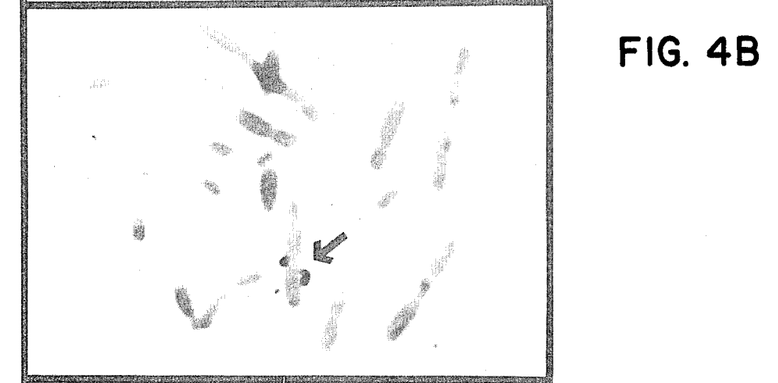
Figure 4C:
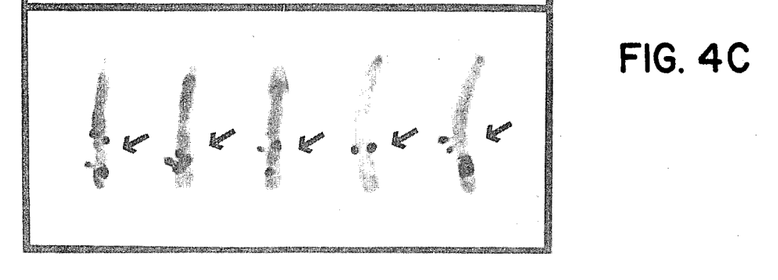

Karyotypic features of gene amplification observed in a number of systems are chromosomal homogeneously straining regions (HSRs) or the presence of double minute chromosomes (DMs) observed in metaphase cells. Such features are known in multidrug-resistant cell lines. In DNA-mediated transfectant cells, the number of DMs correlates with colchicine and multidrug resistance, and the degree of expression of P-glycoprotein. In the CHO cell system, an extensive HSR is observed in $CH^RB30$ cells as shown in FIG. 4, which is not found in the drug-sensitive parental cell line. This region is variable in length, occasionally being almost the size of the Z4 chromosome on which it is located. In order to determine if the amplified P-glycoprotein sequences in $CH^RB30$ cells were contained within this HSR, in situ hybridization was performed using $^3H$-labelled pCHP-1 probe. Of 25 cells examined, 20 yielded one or more autoradiographic grains localized to the HSR of chromosome Z4 as shown in FIGS. 4b and 4c. When total chromosomal grains are scored, 45% (60/133) of all grains are localized to the HSR. In contrast, no significant grain localization was apparent in 25 cells examined using the drug-sensitive parental line AuxBl, the data for which is not shown in FIG. 4.

Characterization of one or more of the genes of the gene family coding for the polypeptide of the P-glycoprotein is accomplished in accordance with the above discussed procedures using the isolated portions of cDNA. The DNA sequence for coding the polypeptide moiety of P-glycoprotein is of approximately 5 kb pairs. This DNA or any segment thereof can be used in a variety of ways to investigate multidrug resistance of cells. Furthermore, one or more genes of the family or a segment of any one of the genes of the family may be used as DNA probes to determine the existence of multidrug resistance in a living cell. The gene or a segment thereof can be incorporated into a suitable vehicle in the manner discussed and transformed into a suitable host to produce the P-glycoprotein or a portion thereof.

Preferred embodiments of the methodology in arriving at the invention will be exemplified in accordance with the following Examples, which are not intended to in any way limit the scope of the appended claims.

EXAMPLE 1

Total cellular RNA was isolated from the highly colchicine resistant CHO cells, B30 according to Chirgwin et al *BIOCHEMISTRY* 18, 5294–5299 (1979). Poly A+RNA was selected from this by chromatography on oligo dT-cellulose (Type 3, Collaborative Research) according to Aviv, H. and Leder, P., *Proc. Natl. Acad. Sci. U.S.A.* 69, 1408–1412 (1972). The product of this step was used as a template for the synthesis of cDNA employing oligo-dT as a primer. 1 μg of poly A+RNA was heated to 70° C. for 5 min., chilled on ice and then incubated for 1 hr. at 42° C. in 50 mM Tris-HCl, pH 8.3, 40 mM KCl, 8 mM $MgCl_2$, 0.4 mM DTT, 0.5 μg oligo dT (12–18; Collaborative Research), 2 mM each deoxynucleotide, 1 μl of $\alpha[^{32}P]dCTP$ (Amersham, 800 Ci/mmol) and 5 units of AMV reverse transcriptase (purified by Sephacryl S-200 chromatography). Second strand synthesis was performed at 14° C. for 5 hr. in the presence of 100 mM HEPES, pH 6.9, 200 mM KCl, 0.2 mM of each deoxynucleotide and 2 μg of homogeneous DNA polymerase 1. Following Sephadex G-100 chromatography in 1 mM Tris-HCl, pH 7.5, 10 μM EDTA, the double stranded cDNA-containing fractions detected by Cherenkov radiation were pooled and lyophilized. The hairpin loop was digested with a 1000 U of S1 nuclease (Boehringer-Mannheim) for ½ hr. at 34° C. Following phenol/chloroform extraction the Sephadex G-100 chromatography step was repeated. Methylation at EcoRl sites was performed after dissolving the pooled, lyophilized fractions in 40 mM Tris-HCl, pH 7.5, 1 mM EDTA, 5 mM DTT, 10 μM S-adenosyl methionine. Incubation with EcoRl methylase (0.1 μ) was at 37° C. for 15 min. Blunt ends were formed by addition of $MgCl_2$ to 10 mM and all deoxynucleotides to 20 μM. After adding 0.25 μg of homogeneous DNA polymerase 1, incubation was at room temperature for 10 min. The Sephadex G-100 desalting step was repeated and peak fractions pooled and lyophilized prior to link addition. Eco Rl linkers (12 mer; Collaborative Research) were phosphorylated before use by the incubation of 3 μg for 1 hr. at 37° C. in 10 mM Tris-HCl, pH 7.5, 10 mM $MgCl_2$, 10 mM ATP and 6 U of 4 polynucleotide kinase (Boehringer-Mannheim). $\gamma-[^{32}P]ATP$ was included so that the reactivity of the phosphorylated linkers could be tested in a trail ligation, the products of which were monitored by electrophoresis in a 10% polyacrylamide gel. The blunt ended cDNA was then resuspended in 5 μl of the phosphorylated linkers (0.5 μg) for ligation overnight at 12° C. by 0.3 μg of homogeneous T4 ligase. EcoRl digestion was performed for 1 hr at 37° C. in 25 mM Tris-HCl, pH 7.5, 100 mM NaCl, 5 mM $MgCl_2$ with 1 unit of homogeneous EcoRl. The cDNA was fractionated on a Sephacryl S-100 column (2mm×15cm in 1 mM Tris-HCl, pH 7.5, 10 μM EDTA). Fractions constituting the leading edge of the cDNA peak were pooled and lyophilized. This material (approximately 30 ng) was annealed with 1 μg of λgtll DNA which has been digested with EcoRl and then treated with calf intestine alkaline phosphatase (Boehringer-Mannheim) till the control packaging efficiency was reduced from $10^7$ to $10^5$ phage per μg. Ligation then proceeded overnight at 10° C. with 0.1 μg of homogeneous T4 ligase. In vitro packaging was performed according to Protocol II of Maniatis, T., Fritsch, E. F. and Sambrook, J., *Molecular Cloning*, Cold Spring Harbor Laboratory, New York, (1982), using extracts prepared as described therein. Plating a bacterial strain Y1090 indicated $1.3 \times 10^6$ recombinants, 65% of which contained cDNA inserts as determined by inactivation of β-galactosidase.

For screening, 600,000 members of the amplified library were plated on strain Y1089 at a density of 100,000 per 15 cm plate and grown at 42° C. for 3 to 4 hours. Nitrocellulose filters (BA85, Schleicher and Schuell) previously soaked in 10 mM IPTG (isopropyl thiogalactoryranoside) and dried were overlaid on the plates and incubation continued for 2 hr. at 37° C. to allow synthesis of the induced β-galactosidase fusion protein. The filters were removed, washed for 3×10 minutes in PBS and allowed to dry for 1 hr. at 37° C. The dried filters were incubated in 3% BSA for 4–6 hr. at 37° C. Filters were transferred to a fresh solution of the same composition containing redioiodinated (~10 uCi/μg) monoclonal antibody C219 and incubated at 23° C. for 10 hr. Ten minute washes were performed sequentially as follows: two times in PBS, two times 0.1% NP 40 in PBS and three times in PBS. After drying, the filters were autoradiographed. The positives detected in the primary screen were carried through several steps of plaque purification to obtain a homogeneous population of positive phage.

EXAMPLE 2

In order to visualize and determine the size of the fusion protein synthesized as a result of insertion of the P-glycoprotein cDNA sequence into the β-galactosidase gene of λgtll, the recombinant phage was grown lytically on strain Y1089. These cells were infected with the λgtll recombinant phage and plated at low density (about 100 per plate) at 32° C. To test for temperature sensitivity, cells from single colonies were spotted onto two plates and one incubated at 42° C., the other at 32° C. Clones which grew at 32° C. but not 42° C. were then used to inoculate 100 ml of LB. After growth at 32° C. until $OD_{600}=0.5$, the temperature was rapidly increased to 43° C. and incubation continued for 20 minutes. IPTG was added to 10 mM and incubation continued at 37° C. for 1 hr. to allow accumulation of induced fusion protein. Cells were harvested by centrifugation at 25° C., resuspended in 1/50 the original volume of PBS and frozen in liquid nitrogen. After thawing, samples were sonicated briefly and electrophoresed on 6.5% polyacylamide gels which were then stained with Coomassie brilliant blue or immunoblotted employing monoclonal antibodies.

Figure 1:
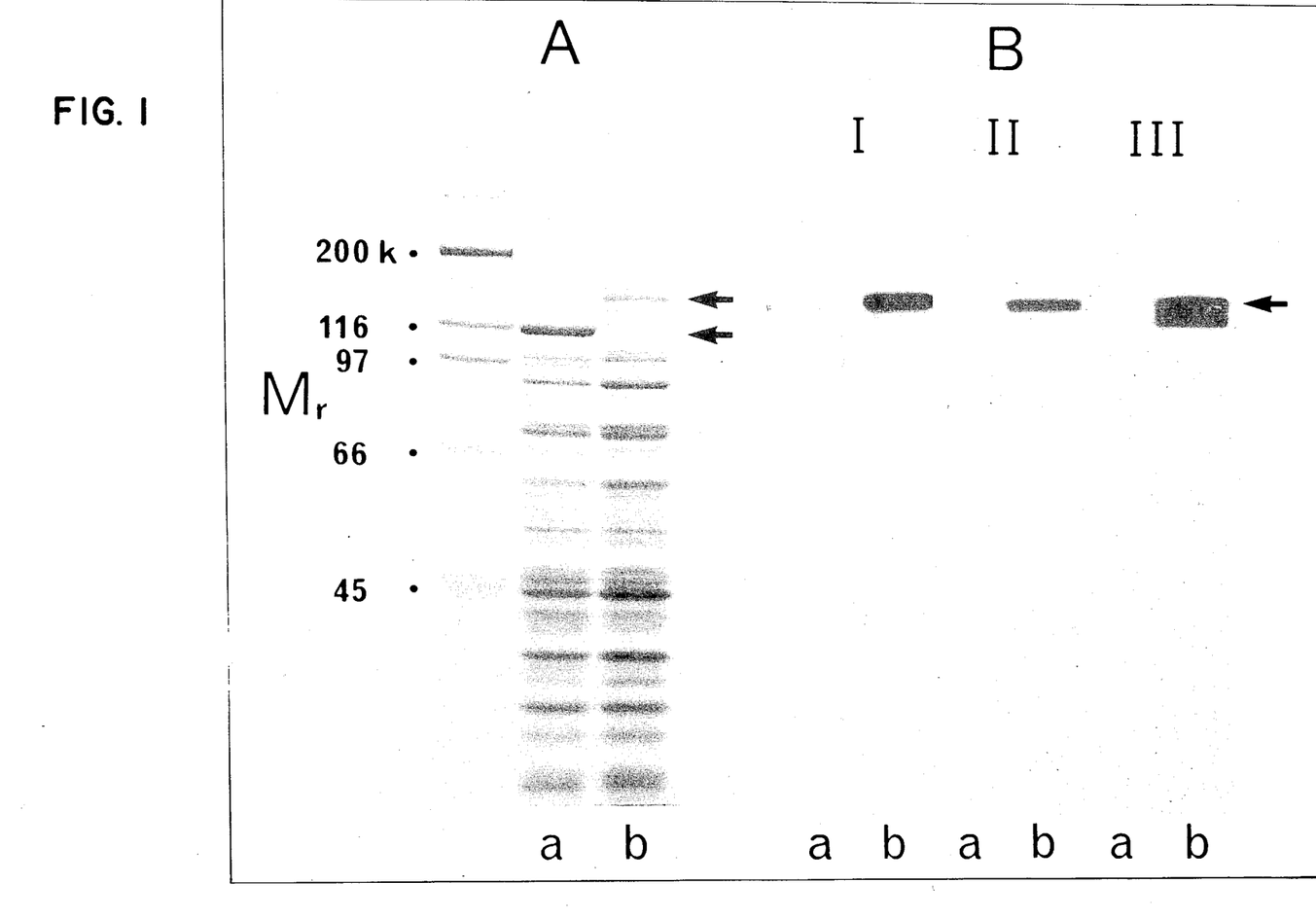
FIG. 1 is the identification and isolation of a cDNA sequence corresponding to a portion of the P-glycoprotein, employing three monoclonal antibodies. Panel A shows the stained fusion protein with a molecular size of 140,000 daltons. Panel B shows the reactivity of this fusion protein with the monoclonal Ab(C219) used to identify the clone and two other monoclonals specific for P-glycoprotein.

With reference to FIG. 1, Panel A is aliquots containing 75 μg protein from lysates of Y1089 bacteria infected with λgtll (lane a) or λCHP-1 (lane b). Molecular weight markers in far left lane were as described previously. Arrows indicate lacZ fusion product of λCHP-1 (top arrow) and uninterrupted β-galactosidase (bottom arrow). Panel B are Western blots of lanes shown in Panel A. Monoclonal antibodies were isolated, and have been classified into three groups on the basis of their ability to recognize three different epitopes on the P-glycoprotein molecule. Three identical sets of blots were probed with representative monoclonal antibodies of Group I (left lanes, C219 probe), Group II (middle lanes, C32 probe) and Group III (right lanes, C494 probe). Lane a, control lysate (λgtll); lane b, lacZ fusion productcontaining lysate (λCHP-1). Arrow indicates expected position of lacZ fusion product. The staining of lacZ fusion product with antibodies identifies three independent epitopes.

The plasmid (pCHP-1) or its insert of approximately 600 base pairs can be used as a DNA probe for molecular hybridization analysis of RNA and DNA from drug resistant and drug sensitive cells; for example, in accordance with the DNA probe technique commonly referred to as the Northern and Southern blot tests.

EXAMPLE 3

A comparison of mRNA homologues to the λCHP-1 phage was undertaken using drug sensitive AuxBl cells and highly drug resistant B30 cells. The results are shown in FIG. 2a.

RNA was isolated from monolayer cultures of cells by disruption in guanidinum thiocyanate and CsCl gradient centrifugation. Agarose (1%) gel electrophoresis, transfer to nitrocellulose (BA85, Schleicher and Schuell) and hybridization was according to Thomas. P. S., in Meth. Enzymol, (eds Wu, R., Grossman, L., Moldove, K.) Academis Press, New York, 100, 255–266 (1983). 15 μg samples of total RNA were dissolved in 1M deionized glyoxal, 50% DMSO, 10 mM sodium phosphate, pH 6.8 and denatured for 1 hr at 50° C. After chilling, sample buffer (50% glycerol, 10 mM Na phosphate and bromphenol blue) was added and electrophoresis carried out for about 6 hr at 90 V with recirculation of the buffer. For transfer, the gel was placed on Whatman 3 MM filter paper soaked in 20×SCC. Nitrocellulose was wetted with water, placed on the gel and covered with 3 mm paper. After blotting for about 10 hr the nitrocellulose was dried under a lamp and baked for 2 hr at 80° C. in a vacuum oven.

The insert corresponding to the portion of P-glycoprotein identified from the λgtll library by monoclonal antibody C219 was prepared for use as a hybridization probe by subcloning into the EcoRl site of plasmid pUC9. The recombinant plasmid thus obtained was termed pCHP-1 and employed directly as a hybridization probe or as a source of insert to be used as probe.

Prehydridization of the Northern blot was at 42° C. for 16 hr in 50% formamide, 5×SCC, 50 mM sodium phosphate, pH 6.5, 250 μg/ml of sonicated salmon sperm DNA, 0.02% BSA, 0.02% Ficoll and 0.02% polyvinyl pyridone. For hybridization 10% dextran sulfate was added. The insert from pCHP-1 labelled by nick translation, was denatured at 100° C. for 5 min. before use for hybridization at 42° C. for 18 hr. Washing was as follows: 4 times 5 minutes in 2×SSC, 0.1% SDS at 23° C. and two times in 0.1×SSC, 0.1% SDS at 50° C. The washed sheet was autoradiographed to yield the pattern shown in FIG. 2a. 28S and 18S indicate the positions of the ribosomal RNAs.

From the Northern blot analysis, it is seen in FIG. 2a that a single major messenger RNA component is observed in the B30 cells in greatly increased amounts with a molecular size of just slightly less than 5 kilobases. Both the increased expression and size of the mRNA revealed by the pCHP-1 probe is completely consistent with the pCHP-1 containing sequences complementary to the P-glycoprotein gene. The protein moiety of P-glycoprotein is about 140,000 daltons which requires a mRNA with a minimum of about 3.5 to 4.0 kb of coding region. It appears that the 5' and 3' untranslated sequences increase the size of the P-glycoprotein mRNA to that of the band in FIG. 2a which is approximately 5.0 kb.

EXAMPLE 4

As mentioned above, cell lines of increased colchicine resistance have increased P-glycoprotein expression. pCHP-1 was used as a hybridization probe to determine if such a relationship also exists for the amount of P-glycoprotein mRNAs in these lines. FIG. 2b shows a slot blot from mRNA prepared from a series of CH clones of increasing drug resistance, namely AuxBl→$CH^RA3$→$CH^RB3$→$CH^RC5$ up to B30 and a revertant clone I10 which was selected from $CH^RC5$. The slot blot apparatus (similar to that of Schleicher and Schnell) was first soaked in 200 μg/ml denatured salmon sperm DNA in 1M ammonium acetate for 2 hr and rinsed with 1M ammonium acetate. The nitrocellulose onto which RNA was to be blotted was soaked in H$_2$O and the 20×SSC as was the underlay of Whatman 3 MM. 200 μl of 20×SSC was loaded onto each slot and allowed to absorb through the underlay. RNA samples (15 μg) prepared as in FIG. 2a after denaturing in glyoxal were diluted to 200 μl with, were loaded and washed in with a further 200 μl of 20×SSC. The apparatus was disassembled and the nitrocellulose, dried, baked and hybridized with pCHP-1 as in FIG. 2a.

The clonal lines CH$^R$A3, CH$^R$B3, CH$^R$C5 were derived in sequential selections for colchicine resistance. CH$^R$B30 was obtained by growing CH$^R$C5 in increasing colchicine concentrations starting from 5 ug/ml in several steps to 30 μg/ml. Revertant I10 was selected from CH$^R$C5 in a single step. Relative resistance to colchicine was determined by the amount of drug required to reduce relative colony forming ability to 10% compared with that required for the parental line.

It can be seen that the amount of mRNA revealed by the pCHP-1 probe in these lines is completely consistent with the pCHP-1 sequences encoding a portion of the P-glycoprotein gene. Taken together, all the above data provides evidence that a fragment of the cDNA is cloned for P-glycoprotein.

EXAMPLE 5

Southern blot analysis of genomic DNA from the drug sensitive and highly multidrug resistant CHO cell lines is shown in FIG. 3a. Fifteen μg of DNA from each cell was digested to completion with EcoR1 and electrophoreses in 0.6% agarose gels. Transfer to nitrocellulose was performed essentially as described by Southern, E. M. *J. Mol. Biol*, 98, 503–517 (1975). The filters were prehybridized 9 hr at 40° C. in 50% formamide, 5×SCC, 20 mM sodium phosphate, pH 6.5, 200 μg/ml of sonicated salmon testes DNA, 0.1% BSA, 0.1% Ficoll and 0.1% polyvinylpyrrolidone. Hybridization of the filters was in the same solution, with the addition of dextran sulfate to 10%. the probe pCHp-1 was prepared by nick translation with [α-[32]p] dCTP to a specific activity of 3×10$^8$ dpm/μg and was added to the hybridization mix after 5 min at 100° C. to a concentration of 10$^6$ cpm/ml. After hybridizing for 35 hr at 40° C., the filters were washed 2 times 5 min in 2×SCC, 0.1% SDS at room temperature, 2 times for 30 min in 2×SCC, 0.1% SDS and 0.1% sodium pyrophosphate at 50° C., air dried and autoradiographed for 15 hr at −70° C. with intensifying screens. Molecular weights were determined from Hind III-digester λ DNA which was co-electrophoresed. AuxB1 (X12) represents the AuxB1 lane exposed 12 times longer. Band 1 in AuxB1 is underrepresented in this experiment. In other experiments, its intensity is similar to band 3 of AuxB1.

From the above, it appears that there are twelve bands of EcoR1 fragments ranging from 1 to approximately 13 kbp in drug sensitive cells. Multiple bands are also observed when other restriction enzymes are used. Since the pCHP-1 probe has no internal EcoR1 sites, and since the insert size is only about 600 bp, the multiple bands observed are indicative of a family of nucleic acid sequences coding for the P-glycoprotein gene in CHO cells. These sequences are amplified in the drug resistant cell line B30. This indicates that the over-expression of P-glycoprotein in this line at the protein and mRNA levels results from gene amplification. The fact that the bands are apparently differentially amplified indicates the P-glycoprotein is encoded by a family of genes. Of interest is the observation of additional amplified bands in B30 DNA not represented by AuxB1 DNA (X12).

EXAMPLE 6

Southern blot analyses of DNAs from other multidrug resistance lines are shown in FIG. 3b. DNA was prepared from drug-sensitive (S) or multidrug-resistant (R) lines and Southern blot analysis undertaken under the same conditions as in FIG. 3a. Autoradiography was for 7 days except in the resistant mouse line (X0.1) where an exposure for 15 hr is also shown. The resistant mouse cell line was derived from L cells and was selected with colchicine. The resistant human cell line was derived from the human leukemic cell line CCRF-CEM and selected for high resistance to vinblastine.

In mouse cells, a family of bands is observed different from that observed in the CHO cells. In the drug-sensitive line, some of the bands are significantly fainter than others. In the human cells, six bands are noted. In the drug-resistant lines, bands observed in the drug sensitive cells are presented in increased copy numbers and in both the human and the mouse systems, differential amplification is observed. In the human system, some of the bands are greatly enhanced in the highly resistant line relative to the sensitive line, whereas others are not.

These observations demonstrate the P-glycoprotein is encoded by a gene family and, that amplification of members of this family is associated with over-expression of P-glycoprotein.

EXAMPLE 7

Cytological evidence for localization of P-glycoprotein sequences to a homogeneous staining region at the Z4 chromosome of CH$^5$B30 cells is shown in FIGS. 4a, 4b and 4c. In FIG. 4a, is a representative G-banded CH$^R$B30 cell demonstrating an HSR on chromosome Z4 (arrow). Such as HSR is not observed in the drug-sensitive AuxB1 line. In FIG. 4b, the results of localization of autoradiographic grains to the Z4-HSR region (arrow) following hybridization in situ with $^3$H-labelled pCHP-1. In FIG. 4c, are examples of grain localization, the Z4-HSR (arrows) are from five different CH$^R$B30 cells as in FIG. 4b.

The results of FIG. 4 were generated by G-banding and in situ hydridization analysis performed as described Trent, J. M., Olson, S., Lawn, R. M. *Proc. Natl. Acad. Sci. U.S.A.* 79, 7809–7813 (1982) and Schwab, M., Alitalo, J., Klempnauer, K-H., Varmus, H. E., Bishop, M. J., Gilbert F., Brodeur, G., Goldstein, M. and Trent, J. M. *Nature* 305, 245–248 (1983). The most consistent and characteristic chromosomal alteration between the parental line AuxB1 and highly colchicine-resistant CH$^R$B30 line is the presence of an HSR on the long arm of the Z4 chromosome as shown in FIG. 4a. In the in situ hybridization procedure, cells were hybridized for 15.5 hr at a final DNA concentration of 0.65 μg ml, followed by exposure for 7 days prior to autoradiographic development as in FIGS. 4b and 4c. The autoradiographic analysis was performed with unbanded chromosomes; however, the size and arm length ratio of the Z4-HSR allowed it to be unequivocally identified in CH$^R$B30 cells.

According to this invention, over-expression of P-glycoprotein genes in the multidrug resistance lines is accompanied by gene amplification. The recent observation that over-expression of P-glycoprotein does occur in advanced ovarian tumour cells suggests that this mechanism is also operative in human malignancies. Since gene amplification featuring HSRs is commonly observed in malignant diseases, it is possible that multidrug resistance mutations may be relatively common and that such mutations may limit successful combination chemotherapy.

The selection of cells having the P-glycoprotein in their membranes resulting in the isolation of a nucleic acid sequence coding for a polypeptide portion of the P-glycoprotein, provides a variety of uses. The mRNA identified by hybridization with the cDNA is of about 5.0 kb in size and the amount is in direct relation to the amounts of the protein and the degree of multidrug resistance in the cell. The cDNA may be used as a DNA probe to recognize P-glycoprotein sequences in human and animal cells and determine amplification of these genes in multidrug resistance. P-glycoprotein genes constitute a multi-gene family, the members of which may be differentially amplified.

Some of the gene sequences for the P-glycoprotein are transferrable to drug sensitive cells when resistance is transferred by transfection with genomic DNA from resistant cells.

The complementary DNA can be used to identify and isolate functional gene sequences of both the cDNA and genomic DNA. Functionality can be monitored by the quantitation of drug resistance after transfection with the cloned sequences. In addition to the development of the primary drug resistance function, these transfection experiments can be used to study the regulation of plasma membrane permeability and transport of large and small molecules. The cDNA probe can be used in the diagnosis of the development of multidrug resistance in cancer patients. This detection capability provides a basis for improved chemotherapy regimes. Furthermore, the system can be used in the detection of tumour cells with amplified P-glycoprotein genes to enable the targeting of chemotherapeutic agents directly to those tumour cells.

Although preferred embodiments of the invention have been described herein in detail, it will be understood by those skilled in the art that variations may be made thereto without departing from the spirit of the invention or the scope of the appended claims.

The embodiments of the invention in which an exclusive property or privilege is claimed are defined as follows:

1. An essentially pure DNA molecule which codes for a polypeptide moiety of a P-glycoprotein having a molecular weight of approximately 170,000 daltons, said P-glycoprotein being a major determinant in multidrug resistance of living cells.

2. An essentially pure DNA molecule of claim 1, wherein said DNA molecule comprises a gene of a gene family which codes for said polypeptide moiety of corresponding P-glycoproteins.

3. An essentially pure DNA molecule of claim 2, wherein said gene family comprises a plurality of genes.

4. An essentially pure DNA molecule of claim 3, wherein said plurality of genes are arranged in tandem array in an amplicon.

5. An essentially pure DNA molecule of claim 3 or 4, wherein said plurality of genes comprises up to ten genes in rodents.

6. An essentially pure DNA molecule of claim 3, wherein said plurality of genes comprises up to eight genes in humans.

7. An essentially pure nucleotide sequence of said DNA molecule of claim 1, wherein said nucleotide sequence codes for a corresponding polypeptide sequence of said P-glycoprotein.

8. An essentially pure nucleotide sequence of claim 7 comprises cDNA.

9. A method of isolating in a plasmid said cDNA of claim 8 comprising constructing a cDNA library using a known phage expression vector and mRNAs obtained from highly drug-resistant cell lines which over-express said P-glycoprotein, identifying recombinant phage vectors which express a fusion protein antigenic to an antibody which is specific to said P-glycoprotein, forming a recombinant plasmid from identified phages, expressing said plasmid in a compatible living cell to produce a corresponding polypeptide sequence, and confirming by use of said antibody that said polypeptide is a portion of said P-glycoprotein.

10. A method of claim 9, wherein said phage is a bacterial phage.

11. A method of claim 10, wherein said phage is λgtll.

12. A method of claim 11, wherein said plasmid is pUC9.

13. An essentially pure nucleotide sequence of claim 7 comprises mRNA.

14. An essentially pure nucleotide sequence of claim 13, wherein said mRNA is of approximately 5 kb and has a coding region for said P-glycoprotein of approximately 4 kb which codes for a protein moiety of approximately 140,000 daltons for said P-glycoprotein.

15. An essentially pure nucleotide sequence of claim 7 comprises a fragment of DNA of said sequence which codes for a corresponding portion of said polypeptide sequence of said P-glycoprotein.

16. A cloning vehicle comprising a bacterial phage in recombinant form with an essentially pure nucleotide sequence of claim 15.

17. A cloning vehicle comprising a plasmid in recombinant form with an essentially pure nucleotide sequence of claim 15.

18. A host cell comprising a cloning vehicle of claim 17.

19. A method of producing a polypeptide sequence which is a fragment of a P-glycoprotein having a molecular weight of approximately 170,000 daltons comprising culturing a microorganism of claim 18 in an aqueous nutrient medium and isolating said polypeptide.

20. A microorganism comprising a cloning vehicle of claim 17.

21. An E. coli microorganism of claim 20 having ATCC accession No. 39839 and comprising said cloning vehicle of claim 17.

22. A method of producing a polypeptide sequence which is a fragment of a P-glycoprotein having a molecular weight of approximately 140,000 daltons comprising culturing a microorganism of claim 21 in an aqueous nutrient medium and isolating said polypeptide.

23. An essentially pure nucleotide sequence of claim 15 in recombinant form with a bacterial phage.

24. An essentially pure nucleotide sequence of claim 23, wherein said bacterial phage is adapted for use as a DNA probe.

25. An essentially pure nucleotide sequence of claim 15, in recombinant form with a plasmid.

26. An essentially pure nucleotide sequence of claim 25, wherein said plasmid is adapted for use as a DNA probe.

27. An essentially pure nucleotide sequence of claim 26, wherein said DNA probe is labelled with a detectable marker.

28. An essentially pure nucleotide sequence of claim 27 wherein said marker is radioactive.

29. An essentially pure nucleotide sequence of claim 23, wherein said marker is fluorescent.

30. An essentially pure nucleotide sequence of claim 27, wherein said marker is biotinylated.

31. An essentially pure nucleotide sequence of claim 15, wherein said DNA fragment is approximately 600 base pairs.

32. An essentially pure nucleotide sequence of claim 31, wherein said DNA fragment is cDNA.

33. An essentially pure nucleotide sequence of claim 32 which codes for a polypeptide sequence having three different epitopes specific to said P-glycoprotein as indicated by three different antibodies raised to said P-glycoprotein.

34. An essentially pure nucloetide sequence of claim 15, wherein said DNA fragement is approximately 2,500 base pairs.

35. An essentially pure DNA molecule of claim 1, wherein said molecule is derived from Chinese Hamster Ovary cells.

36. An essentially pure DNA molecule of claim 1, wherein said molecule is derived from mouse cells.

37. An essentially pure DNA molecule of claim 1, wherein said molecule is derived from human cells.

* * * * *